United States Patent [19]
Knowlton

[11] Patent Number: 5,937,863
[45] Date of Patent: Aug. 17, 1999

[54] SURGICAL METHOD FOR BREAST RECONSTRUCTION USING A TISSUE FLAP

[76] Inventor: Edward J. Knowlton, 5478 Blackhawk Dr., Danville, Calif. 94506

[21] Appl. No.: 08/887,668

[22] Filed: Jul. 3, 1997

Related U.S. Application Data

[62] Division of application No. 08/408,599, Mar. 22, 1995, Pat. No. 5,765,567.

[51] Int. Cl.$^6$ ....................................................... A61F 2/12
[52] U.S. Cl. .............................. 128/898; 128/897; 623/8; 623/66
[58] Field of Search ................................... 128/898–899, 128/897; 623/8, 66

[56] References Cited

U.S. PATENT DOCUMENTS

| 5,301,692 | 4/1994 | Knowlton | 128/898 |
| 5,765,567 | 6/1998 | Knowlton | 128/898 |
| 5,824,076 | 10/1998 | Knowlton | 623/8 |

OTHER PUBLICATIONS

M. Anton et al., "Nipple Reconstruction With Local Flaps: Star and Wrap Flaps", *Perspectives in Plastic Surgery*, 5:67–78 (1991).

J. Bostwick et al., "Breast Reconstruction After a Radical Mastectomy", *Plastic and Reconstructive Surgery*, 61:682–693 (May 1978).

P. Grossman et al., "An Alternative Technique for Modified Radical Mastectomy with Immediate Reconstruction", *Contemporary Surgery*, 36:20–24 (Jun. 1991).

E. Knowlton, "Release of Axillary Scar Contracture with a Latissimus Dorsi Flap", *Release of Axillary Scar Contracture*, 74: 124–126 (Jul. 1983).

G. Maxwell, M.D., "Iginio Tansini and the Origin of the Latissimus Dorsi Musculocutaneous Flap", *Plastic and Reconstructive Surgeons* 65:686–692 (May 1980).

W. Schneider et al., "Latissimus Dorsi Myocutaneous Flap for Breast Reconstruction", *British Journal of Plastic Surgery*, 30:277–281 (1977).

*Primary Examiner*—Jeffrey R. Jastrzab
*Assistant Examiner*—Ryan Carter
*Attorney, Agent, or Firm*—Wilson Sonsini Goodrich & Rosati

[57] ABSTRACT

A procedure for breast reconstruction with a tissue flap having a cutaneous skin island. The procedure is performed as a total, immediate reconstruction, or on a delayed basis of reconstruction. The tissue flap is a free flap or a flap attached via a native vascular pedicle. Forces acting on the skin island yield enhanced nipple-areolar projection of the reconstructed-breast.

16 Claims, 9 Drawing Sheets

SURGICAL METHOD FOR BREAST RECONSTRUCTION USING A TISSUE FLAP

This application is a division of Ser. No. 08/408,599 filed Mar. 22, 1995 now U.S. Pat. No. 5,765,567.

TECHNICAL FIELD

The invention relates to a medical procedure, and more specifically to a surgical method that provides an anatomically correct breast reconstruction from a single-stage or multi-stage procedure.

BACKGROUND ART

Cancer of the female breast is a significant health matter worldwide. The current treatment of breast cancer includes surgery, chemotherapy and radiation therapy, and combinations of these three modalities. Approximately one-half of the women in the U.S. that are diagnosed with breast cancer will elect or will require a mastectomy. Thus, mastectomy procedures are commonly used for the treatment of breast cancers.

Mastectomies have been performed since the late 1800s, by a procedure technically known as the Halstead radical mastectomy. During this procedure, the breast tissue and the pectoralis major muscle along with a variable amount of skin including the nipple-areolar complex is removed. Typically, an axillary lymph node dissection is performed concurrently with the mastectomy. This procedure leaves the patient with a Halstead radical mastectomy deformity which is disfiguring and can be emotionally traumatic. The deformity is especially disfiguring when skin drafting is required to close the defect.

The Halstead procedure ("radical mastectomy") has been modified by preserving the pectoralis major muscle (a "modified radical mastectomy"), and by reducing the skin excision to allow for direct linear closure of the defect. As discussed below, mastectomy closure is distinct from post-mastectomy breast reconstruction. Mastectomy closure techniques serve merely to close the excision site, not to reconstruct the shape and aesthetics of a breast.

Post-Mastectomy Closure: In the past, mastectomy closure techniques have included split thickness skin grafts attached directly to the rib cage, in the context of a Halstead radical mastectomy; or simple straight line closure of an elliptical skin excision.

Closure of the skin defect could also involve the immediate incorporation of a cutaneous or myocutaneous tissue flap to at least partially replace the excised tissue. Myocutaneous units are commonly used to cover defects, whether traumatic or post-resectional. Myocutaneous units were prepared as a combination of both skin and muscle, or as a muscle units that subsequently were skin grafted. Myocutaneous units were transferred as free flaps (flaps detached from intrinsic blood supply), thereafter connecting the unit's axial blood supply to recipient vessels near the defect.

Latissimus dorsi or rectus abdominis myocutaneous flaps were the most frequently utilized myocutaneous flaps for post-mastectomy closure. Some common closure applications for latissimus dorsi flaps include coverage of defects in the head and neck area, especially defects created from major head and neck cancer resection; additional applications include coverage of chest wall defects other than mastectomy deformities. The latissimus dorsi was also used as a reverse flap, based upon its lumbar perforators, to close congenital defects of the spine such as spina bifida or meningomyelocele.

To affect post-mastectomy closure, a latissimus dorsi myocutaneous flap procedure was first combined with the Halstead mastectomy by Dr. Iginio Tansini in Italy in 1906. (Maxwell: *Iginio Tansini* and the *Origin of the Latissimus Dorsi Musculocutaneous Flap, Plastic and Reconstructive Surgery* (1980) 65(5):686–692) As illustrated in FIG. 1, a latissimus dorsi myocutaneous flap having a cutaneous paddle P, was used to close the mastectomy defect. This myocutaneous flap had an intrinsic axial blood supply that was critical to the transfer and survivability of the flap.

Prior to the development of the Tansini procedure, random cutaneous flaps had limited survivability due to the paucity of their blood supply. The Tansini procedure did not, however, result in breast reconstruction. The flap was used only to close the chest wall defect.

Post-Mastectomy Breast Reconstruction: Due to the adverse characteristics of a mastectomy deformity, either from a radical mastectomy or a modified radical mastectomy, many women opt for post-mastectomy breast reconstruction. Reconstruction can take place contemporaneously with the mastectomy, or at a later time.

To achieve breast reconstruction, it is common to use a submuscular breast expander or a permanent implant in conjunction with some form of a mastectomy closure technique. A breast expander allows for, and generally requires, sequential addition of fluid to stretch the remaining breast tissue. Accordingly, expanders or implants ("breast inserts") are inserted beneath the mastectomy incision, and have been used as a method for either immediate or delayed breast reconstruction.

Post-Mastectomy Use of Myocutaneous Flaps: There are several disadvantages to post-mastectomy use of former myocutaneous flaps, in the context of excision closure or of post-surgical breast reconstruction. In either of these contexts, most procedures cause a significant transverse scar across the chest. Transverse double tier scarring Ts is illustrated, for example in FIG. 1. The donor site scar on the back is also substantial. When such procedures are used and a breast is reconstructed, the disadvantages are exacerbated since there is a large elliptical paddle of skin across the breast. This skin paddle has different pigmentation than the adjacent breast skin. Furthermore, the large flap of skin does not adequately recreate the contour of the breast.

Circumareolar Mastectomy: Previously, major resections of skin occurred during radical or modified radical mastectomy procedures. More recently, skin resection has been limited to the nipple-areolar complex, through a circumareolar or periareolar incision. Modified radical mastectomies with circumareolar incisions have been performed on patients who did not have pre-existing invasion of the surrounding breast skin. When the skin excision is limited to the region of the nipple-areolar complex, the skin envelope of the breast is preserved.

When a circumareolar mastectomy was performed via an excision of the nipple-areolar complex, a straight line closure with insertion of breast expander has been used. (Grossman et al.: *An Alternative Technique for Modified Radical Mastectomy with Immediate Reconstruction. Contemp. Surg.* (1991) 38(6):20–24) Thus, with this form of post-mastectomy reconstruction the incision was closed with a straight line closure. Consequently, the reconstructed breast was skin deficient in comparison to the contralateral breast. This tissue shortage frequently required a repositioning surgery of the contralateral breast, resulting in scarring on the contralateral breast and on the ipsilateral breast. Moreover, the reconstructed breast lacked any nipple-areolar complex.

Trans-rectus abdominis muscle flaps (TRAM flaps) have also been used in combination with a circumareolar mastectomy. TRAM flaps have served to close a mastectomy defect and to provide breast reconstruction. With the TRAM flap, a circular skin island is designed and transferred to the mastectomy defect. In some instances, a nipple-areolar reconstruction was performed. This skin island did not result in a reconstructed breast having a nipple-areolar complex with the same projection as a normal breast. In a TRAM flap procedure, the subcutaneous tissue of the flap, rather than a breast implant, fills the void left by the removal of the breast tissue. As with other myocutaneous flaps, projection of the nipple-areolar complex was poor. The subcutaneous tissue is primarily adipose tissue; the transferred rectus abdominis muscle functions princi ply as a conduit of the vascular supply. Rather, the majority of the reconstructed breast volume was filled by adipose subcutaneous tissue of the TRAM myocutaneous unit.

A physician and patient must weigh a number of issues when contemplating use of a TRAM flap. The flap loss rate is higher with TRAM flaps as compared to latissimus dorsi flaps, because the circulation of the myocutaneous unit is less reliable. Heretofore, a nipple-areolar reconstruction with circulation sufficient to support harvesting and regrafting of the patient's own areola was not possible due to the poor blood supply with former TRAM flaps. Moreover, there is no reported literature documenting successful contemporaneous post-mastectomy TRAM flap breast reconstruction to provide a breast with-a nipple-areolar complex. Since subcutaneous adipose tissue provides the majority of the reconstructed breast volume with former TRAM flaps, fat necrosis of this tissue was a significant complication with this procedure. If fat necrosis of the adipose tissue occurs, calcifications and connective tissue masses can result. These sequelae can further exacerbate the difficulty of diagnosing a chest wall cancer recurrence, and diminish the quality of the reconstructed breast.

The donor site scar can be an issue with the TRAM procedure: the scar is located on the lower abdomen and runs hip to hip. Patients may be subject to abdominal wall weakness and hernia formation after one or two rectus muscles are transferred to the breast. The TRAM flap procedure can be performed only once. Breast reconstruction for any subsequent breast cancer would require the use of a different technique. Use of a TRAM flap is limited if the woman has any abdominal scars or if the woman has an inadequate amount of subcutaneous tissue. These limiting issues with a TRAM flap were especially problematic when attempting to reconstruct a large breast. However, some women prefer a TRAM procedure, it can often achieve breast reconstruction without use of an implant, and it can serve as abdominoplasty if a woman has excess abdominal tissue.

Former free gluteal flaps have also been designed which function in a similar fashion to the former TRAM flap. The former gluteal flap has the same disadvantages as the former TRAM flap, as well as the disadvantages typically attendant to free flaps.

In general, there are several significant drawbacks with prior breast reconstruction procedures when used after a standard modified radical mastectomy. Severe scarring is one of the most serious problems. Due to the substantial contour distortion produced by these techniques, a reliable method of immediate and total breast reconstruction could not be performed, since it was difficult to determine where the nipple-areolar complex should be placed in a one-stage procedure. Moreover, repositioning of the contralateral breast was often required, consequent to the limited amount of tissue available for reconstruction on the mastectomy side. Thus, at best, multiple stage breast reconstruction procedures were necessary. Each subsequent procedure carried additional surgical risks, such as infection, bleeding, and anesthetic complications. After a breast was reconstructed, the breast had a distinctly artificial appearance due to the large amounts of skin resection and scarring.

DISCLOSURE OF THE INVENTION

Disclosed is a surgical method for breast reconstruction. The method comprises making an incision on a breast, such that the incision defines an incision plane area. A tissue flap is surgically utilized where the cutaneous portion of the flap has a surface area greater than the maximal unstretched incision plane area, or wherein the cutaneous portion has a service area equal to or less than the maximal unstretched incision plane area and further comprising reducing the incision plane area to be less than the area of the cutaneous portion of the flap. The step of surgically utilizing the tissue flap can be contemporaneous with the mastectomy or at a subsequent stage. If the step of surgically utilizing a tissue flap is not contemporaneous with the performing of a mastectomy, the step of providing an incision on the breast is contemporaneous with the surgically utilizing step. An inferior vertical wedge resection or purse string suturing can be used to reduce the incision plane area. If the cutaneous portion of a tissue flap has a surface area greater than maximal unstretched incision plane area, the step of surgically utilizing the flap can comprise stretching the incision so that the maximal area defined by the incision corresponds to the area of the skin of the cutaneous portion of the flap. The invention results in enhanced nipple areolar projection; nipple-areolar projection is further enhanced during the healing process due to scar contraction and elastic recoil forces.

Disclosed is a surgical method comprising the contemporaneous steps of performing a mastectomy on a breast through a substantially circumareolar incision which defines a maximal unstretched incision plane area. A cutaneous flap or a non-latissimus dorsi myocutaneous flap (a myocutaneous flap which is not derived from latissimus dorsi muscle) is surgically utilized in a step that comprises placing the cutaneous portion of the flap within the incision plane area. The flap can have a cutaneous peg which has a surface area greater than the maximal unstretched incision plane area defined by the incision, or the flap can have a cutaneous portion which has a surface area equal or less than the maximal unstretched incision plane area and further comprising reducing the incision plane area so as to be less than the area of the cutaneous portion of the flap. The flap can comprise sufficient vascularization to support a contemporaneous nipple-areolar reconstruction. The method can further comprise the creation of a nipple-areolar complex with a portion of the cutaneous portion of the flap.

Disclosed is a surgical method which comprises the performing of a surgical procedure itself comprising performing a mastectomy. The incision that was utilized to perform the mastectomy is closed. Subsequently, a surgical procedure is performed which comprises surgically utilizing a tissue flap which comprises a cutaneous portion. The cutaneous portion of the tissue flap has a perimeter shape that corresponds in shape to the perimeter of an areolar. The flap is one that routinely supports creation of a nipple-areolar complex. The method can further comprise a step of placing a breast expander; the expander can be placed during the procedure that comprises performing a mastectomy. The step of surgically utilizing the flap can comprise creating a nipple-areolar complex. The surgically utilizing step can comprise creating a substantially circular incision having a shape that corresponds to the perimeter of an areolar. The incision defining a maximal unstretched incision plane area. The cutaneous portion of the tissue flap has a surface area greater than the maximal unstretched incision plane area or has a surface area equal or less than the maximal unstretched incision plane area. If the cutaneous portion is less than the maximal unstretched incision plane area, the method further comprises reducing the incision plane area so as to be less than the area of the cutaneous portion of the flap.

Disclosed is a method for creating an effectively enlarged submuscular compartment for use in a surgical procedure on a breast such as post-mastectomy breast reconstruction or breast implant repositioning. The method comprises placing a subcutaneous breast insert. The insert is removed after a scar capsule has formed around the insert. The scar capsule is attached to a pectoralis major muscle which defines a submuscular space or is capable of defining a submuscular space. Accordingly, an effectively enlarged submuscular department is created. The insert can be a breast implant or a breast expander.

Disclosed is a method for recreating a nipple-areolar complex. The method produces a nipple-areolar complex with conical projection, and comprises dissecting a nipple flap and two rectangular flaps on a tissue flap. The two rectangular flaps are connected at their respective proximal margins to the nipple flap, and the rectangular flaps are connected to the nipple flap on opposite sides of the nipple flap. The nipple flap and the two rectangular flaps are sutured together to create a reconstructed nipple-areolar complex. The proximal end of each rectangular flap is defined as being that end which is attached to the nipple flap. In one embodiment, at least one rectangular flap is wider distally than its width at its proximal connection to the nipple flap. The nipple flap or a rectangular flap can be dissected to comprise subcutaneous tissue to provide increased volume to the reconstructed nipple. The procedure can further comprise circumscribing a perimeter of the reconstructed nipple-areolar complex with a substantially circular template, in order to facilitate obtaining a substantially circular reconstructed complex. Cutaneous tissue beyond the perimeter of the nipple-areolar complex can be dissected.

MODES FOR CARRYING OUT THE INVENTION

Figure 1:
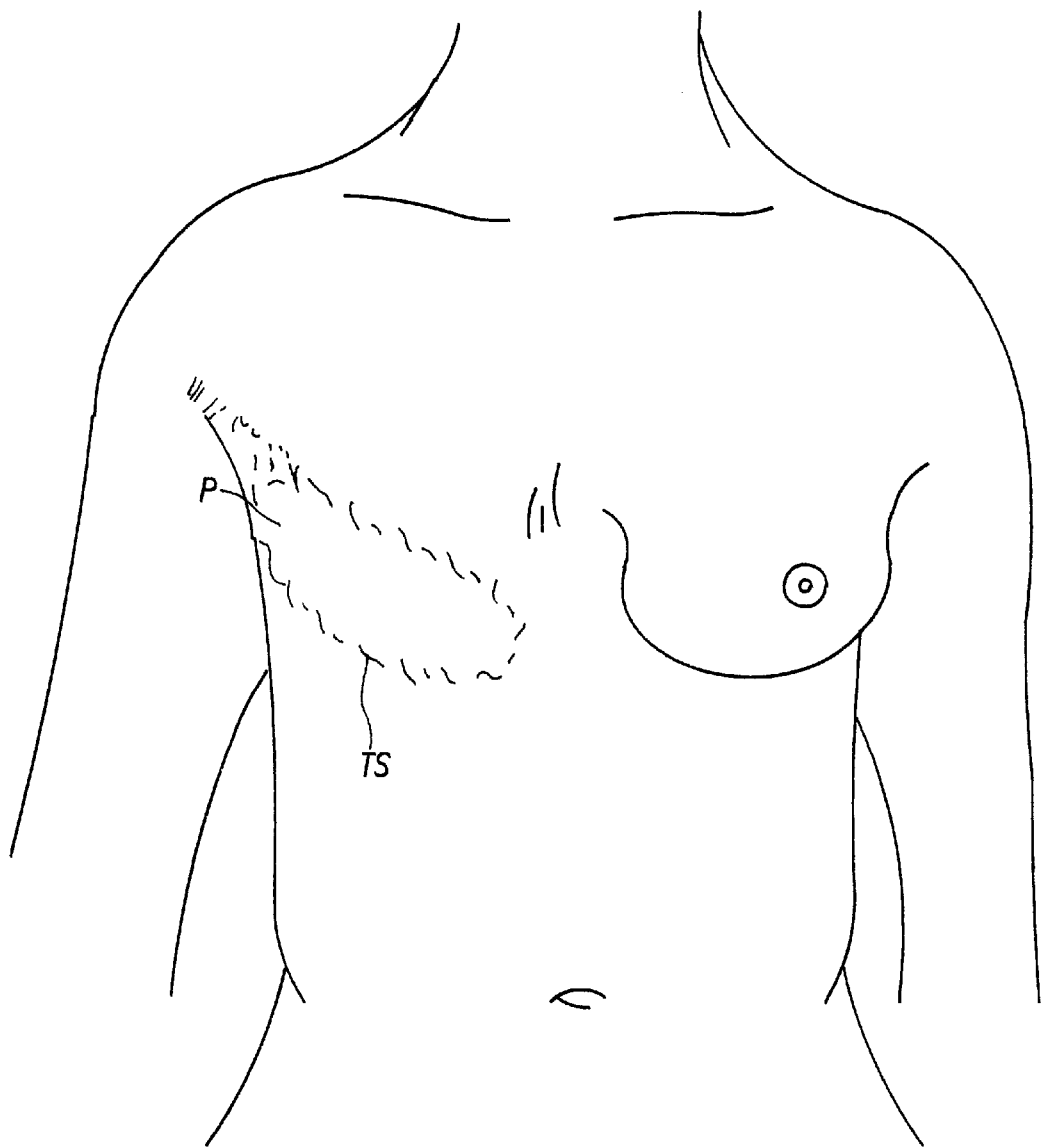
FIG. 1 illustrates a surgical result from a prior art latissimus dorsi reconstructive procedure following a radica astectomy.

As disclosed herein, a tissue flap is used for breast reconstruction whereby a nipple-areolar reconstruction can be performed that results in enhanced nipple-areolar projection. The tissue flap can be a cutaneous flap which comprises cutaneous tissue, subcutaneous tissue and inherent circulatory vessels; or, a myocutaneous flap which comprises muscular tissue, cutaneous tissue, subcutaneous tissue and inherent circulatory vessels. As used herein, cutaneous is defined to mean a fully epithelialized or a partially deepithelialized flap. The flap can be a free flap or a flap where the inherent vessels remain connected with the native blood supply. As defined herein, reconstruction comprises a procedure to provide any change in the shape, volume or contour of a breast. Thus, a reconstruction can be a post-mastectomy procedure, a post-traumatic procedure, or a procedure done to enlarge or decrease the volume of the breast. A reconstruction can be contemporaneous with a mastectomy or can be delayed, taking place over one or more post-mastectomy surgical procedures. In accordance with the invention, a delayed procedure comprises: a multistage procedure where a mastectomy is performed with contemporaneous placement of an expander, and a subsequent procedure when a tissue flap reconstruction is performed; a mastectomy; a subsequent procedure when an expander is placed, and a subsequent procedure when a tissue flap reconstruction is performed; revisions to a previous reconstruction; or, the placing or modifying of breast implant materials. A immediate reconstruction procedure in accordance with the invention comprising use of a latissimus dorsi muscle has been used to particular advantage following a modified radical circumareolar mastectomy. Nothing in the art has disclosed post-surgical reconstruction with any non-latissimus dorsi source following a circumareolar mastectomy. Moreover, as disclosed herein, immediate reconstruction in accordance with the invention can be employed with autologous sources other than the latissimus dorsi and delayed reconstruction can comprise use of a latissimus dorsi. Individual steps of the invention are performed in accordance with standard medical protocol, standard protocols such as the protocol relating to the management of any bleeding or the protocol for prevention of infection.

A tissue flap having a cutaneous peg of dermal and epidermal tissue is used. The tissue flap can be a free flap or a flap connected to its native/intrinsic vasculature. As used herein, a cutaneous peg comprises dermal tissue, and typically comprises epidermal and dermal tissue. The tissue flap can comprise a muscular portion, whereby the flap is termed a myocutaneous flap. Thus, a tissue flap comprises an elevated platform from which a nipple-areolar complex can be reconstructed.

The cutaneous peg is generally circular, and has a rounded configuration that corresponds to the perimeter of an areola. In one preferred embodiment, the peg has a superficial epidermal area that is greater than the maximal unstretched two-dimensional area of the incision opening. (The two-dimensional area of the incision opening can be termed the incision plane area.) This embodiment is typically utilized with delayed reconstruction. In another preferred embodiment of the peg, the peg has a superficial epidermal area that corresponds to or is less than the initial maximal unstretched two-dimensional area of the incision opening. This embodiment is typically used with immediate reconstruction. The embodiment where the peg has a superficial epidermal area that corresponds to or is less than the initial maximal unstretched two-dimensional area of the incision opening, incision perimeter reduction is typically performed. Incision perimeter reduction serves to decrease the maximal unstretched incision plane area, and can comprise pursestring suturing or performing a wedge resection. The preferred peg embodiments lead to a reconstructed nipple-areolar complex with improved projection relative to former reconstructed breasts.

Thus, the invention provides a method for total breast reconstruction that is either delayed or immediate. With an immediate reconstruction, the patient does not experience a mastectomy deformity and accompanying emotional trauma; however, for many women a delayed reconstruction is medically indicated. For patients who have undergone a standard modified radical mastectomy, delayed autologous reconstruction is accomplished after expansion of the skin envelope. With delayed reconstruction, the tissue flap and the nipple-areolar complex are each created in processes that have steps that correspond to the steps which are carried out with an immediate reconstruction.

When a tissue flap with requisite vasculature is used, the patient's own areola can be harvested and incorporated within an immediate nipple-areolar reconstruction. The reconstruction technique of the present invention is appropriate for the complete range of breast sizes, and can be performed bilaterally. Bilateral reconstruction in accordance with the invention can be contemporaneous or sequential.

As used herein, a "substantially circumareolar incision" comprises an incision that circumscribes at the perimeter of the nipple-areolar complex; in instances where a breast reduction and/or a nipple-areolar repositioning is to be performed, an incision that circumscribes at the perimeter of the nipple-areolar complex and includes additional breast skin; and, an incision that approximates the areolar perimeter yet is within the area of the areola. Preferably, particularly for immediate embodiments of the invention, the circumareolar incision closely corresponds to the perimeter of the areola, and is at or within the margin of the areola. A substantially circumareolar incision also comprises radial or wedge skin incisions at the border of the areola. Radial or wedge skin incisions at the border of the areola are less ideal since they create scarring that does not correspond to a natural tissue plane.

Advantageously, a reconstructed breast produced in accordance with the present invention has better contour and projection than reconstructed breasts that resulted from prior procedures.

Preferred embodiments of the procedure of the present invention are performed following a circumareolar mastectomy. A circumareolar mastectomy eliminates the transverse mastectomy scar which was a consequence of prior reconstruction procedures. To make most advantageous use of a circumareolar mastectomy, it is preferred that the surgeon limit any biopsy and subsequent mastectomy skin excision to the region of the nipple-areolar complex. When the skin excision in a mastectomy is limited to the region of the nipple-areolar complex, the skin envelope of the breast is completely preserved. Since the biopsy incision is generally removed at the time of the mastectomy, biopsy incisions outside the region of the areola often necessitate a non-preferredly large skin incision on the breast skin envelope. With a large skin incision, the mastectomy scar is not camouflaged at the border of the areola, and the reconstructed breast is less likely to have a normal contour. Direct tumor involvement of the breast skin is infrequent, skin involvement typically provides an indication for the delayed embodiments of the invention and restricts the applicability of the immediate embodiments of the procedure since a circumareolar mastectomy generally cannot be done.

A mastectomy excision through a substantially circumareolar incision that is larger than the areolar perimeter can be performed in accordance with the invention, particularly for patients for whom a breast reduction and/or nipple-areolar repositioning is indicated; for such patients, a "substantially circumareolar incision" comprises an incision that corresponds to the perimeter of the areola and comprises an incision that corresponds to a standard pattern reduction or repositioning incision. In general, if a skin resection extends beyond the perimeter of the nipple-areolar complex, the resulting mastectomy scar is more readily apparent; the contour and projection of the reconstructed breast will be flatter and less natural.

Alternatively, yet also in accordance with the present invention, a variable amount of areola may be left with the breast skin. In such a situation, for example, the cutaneous peg could then be used to reconstruct only the excised nipple.

Radiation therapy is known to those skilled in the art to be less distorting if performed after a breast reconstruction. Patients necessitating postoperative radiation therapy can be candidates for the procedure of the invention. The procedure will not alter the patient's post-operative prognosis. Size or stage of the breast cancer will not limit applicability of the procedure. If a modified radical mastectomy with a large elliptical skin excision is indicated, a delayed reconstruction in accordance with invention is generally used.

A preferred latissimus dorsi or TRAM myocutaneous flap of the invention differs substantially from a myocutaneous unit in a standard TRAM flap procedure. An immediate and total post-mastectomy reconstruction has not ever been performed with a standard TRAM flap, due largely to the poor circulation present with the standard TRAM flap. There are factors to balance when selecting between a TRAM flap of the invention and a latissimus dorsi flap of the invention. A latissimus dorsi flap has greater circulation and results in a smaller donor site scar than a TRAM flap, a preferred TRAM flap often provides more tissue than a latissimus dorsi flap, the TRAM flap can be used to accomplish diminution of abdominal tissue (effectively a "tummy tuck" procedure), however the there is more donor site morbidity with a TRAM flap than with a latissimus dorsi flap.

By use of preferred embodiments, the present invention can be performed on both breasts. Thus, if a subsequent breast cancer occurs in the contralateral breast, the same procedure can be performed. Alternatively, if a bilateral breast cancer is present, one or both breasts can be reconstructed with this technique. The TRAM embodiment of the invention can be used for contemporaneous bilateral breast reconstruction; the latissimus dorsi embodiment can be used for contemporaneous or non-contemporaneous/sequential bilateral breast reconstruction. As appreciated by one of ordinary skill in the art in view of the teachings of the invention, the invention can comprise use of tissue flaps such as a gluteal flap, lateral thigh flap, and a Reubens flap.

Immediate Reconstruction

A preferred embodiment of the invention will now be described. The patient is initially placed in a lateral decubitus position, so that the breast requiring the mastectomy is raised. Initially, the cutaneous "peg" is marked behind the anterior border of the latissimus dorsi. The chest, back and upper extremities are prepped in a circumferential fashion. This arrangement allows that the patient can be alternately placed between the supine and the lateral decubitus positions without redraping.

The patient is then placed into a supine position on a sterile drape and a circumareolar mastectomy is performed. A mastectomy is performed through a circumareolar incision, such as the procedure of Grossman et al.: *An Alternative Technique for Modified Radical Mastectomy with Immediate Reconstruction. Contemp. Surg.* 38(6):20–24, (1991). It is believed that subcutaneous tissue dissection without cautery results in less damage to the subdermal plexus. Much of the bleeding which is encountered is subcutaneous bleeding, such bleeding can be controlled merely by packing. The nipple-areolar complex is incised circumferentially. The initial periareolar breast biopsy incision is included with the specimen. Sharp dissection without cautery is indicated when raising the skin flap of the breast. As the breast skin exists as a random cutaneous flap, the subcutaneous layer is preserved to avoid damage of the subdermal plexus. The pectoralis fascia can be included with the breast specimen. The lymph node dissection may require a separate axillary incision. If an axillary incision is made, identification of the latissimus dorsi muscle and thoracodorsal vessels is facilitated. An incision is made in the axilla; the incision is of sufficient size to perform axillary lymph node dissection and identify-the latissimus dorsi and teres major muscles and the thoracodorsal artery and vein. (Bostwick, et al.: *Breast Reconstruction After Radical Mastectomy. Plast. Reconstr. Surg.* (1978) 61:682) The nipple-areolar complex, breast tissue, pectoralis fascia and axillary lymph nodes are delivered as an en bloc specimen.

The thoracodorsal vessels and nerve are identified and isolated in the axilla. The branch to the serratus anterior is routinely ligated to improve the arc of rotation of the flap. Dissection of the thoracodorsal vessels to the axillary vein will provide additional length to the pedicle. The subcutaneous fat over the serratus anterior is included with the flap to provide additional breast volume and reduce the typical "fullness" of the lateral chest due to lymphedema from the axillary lymph node dissection.

The patient is then rotated into a lateral decubitus position. In a preferred embodiment, the latissimus dorsi is the source of sufficiently vascularized cutaneous tissue; other sufficiently vascularized musculocutaneous units can also be used. For example, a tissue flap can be derived from the rectus abdominis, or can be a lateral thigh flap, a Reubens flap, or gluteal flap. As appreciated by one of ordinary skill in the art of anatomy based on the teachings of the invention, sufficiently vascularized tissue units are selected, for example, by isolating a cutaneous area from a region served by myocutaneous perforator vessels. The vascularization is preferably sufficient to support immediate nipple-areolar reconstruction. Flaps attached via an intrinsic vascular pedicle as well as free flaps can be used in the surgery; free flaps can be used with immediate reconstruction after standard vascular reattachment of the flap in the reconstruction site.

Figure 2:
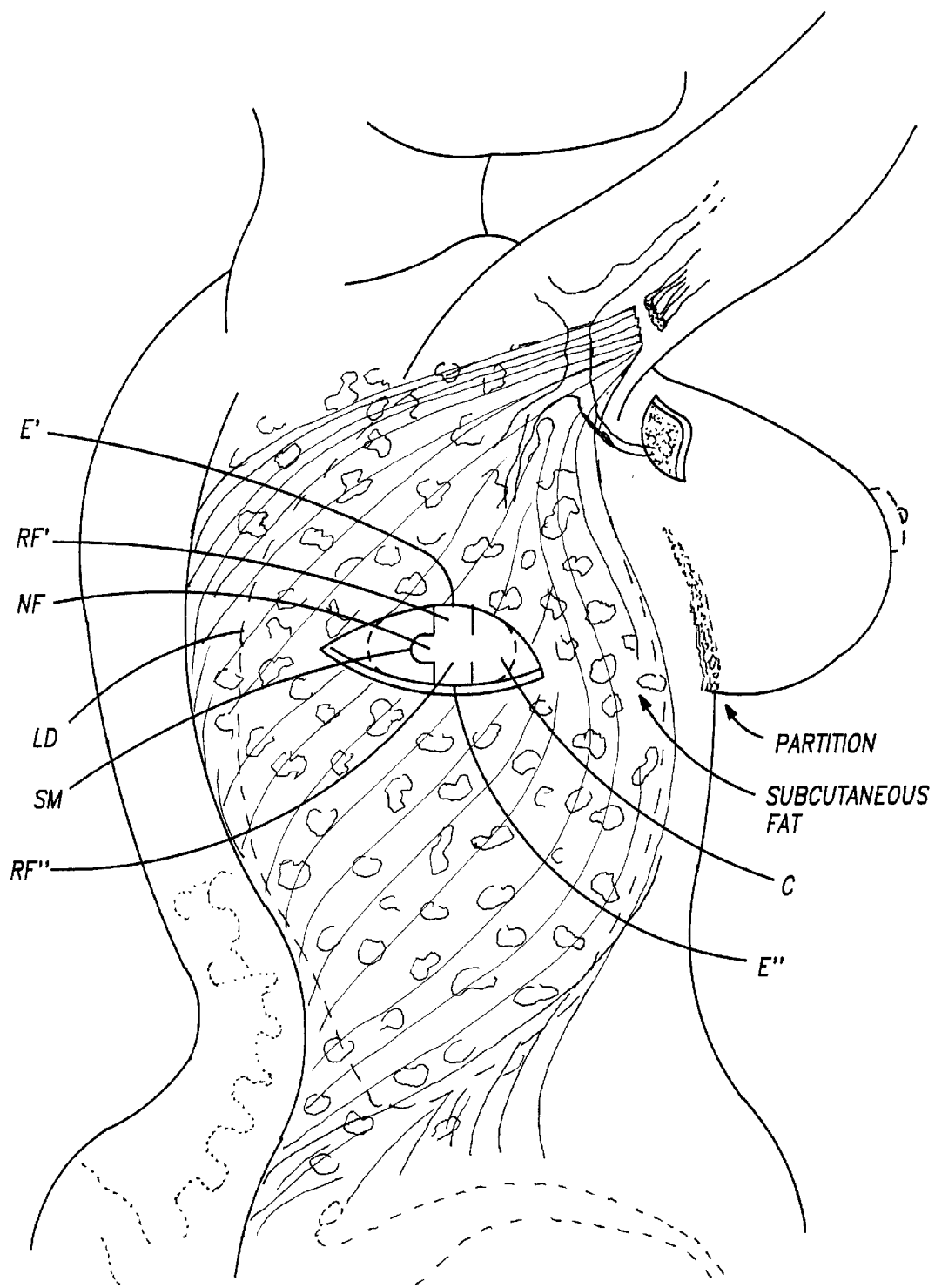
FIG. 2 illustrates a latissimus dorsi muscle, the outline of a latissimus dorsi flap and the cutaneous portion of the flap. The cutaneous portion is shown with the incisions that will produce a semicircular margin (SM), a rectangular flap (RF'), a second rectangular flap (RF") and a nipple flap (NF). The respective ends (E' and E") of the rectangular flaps are depicted.
Figure 3:
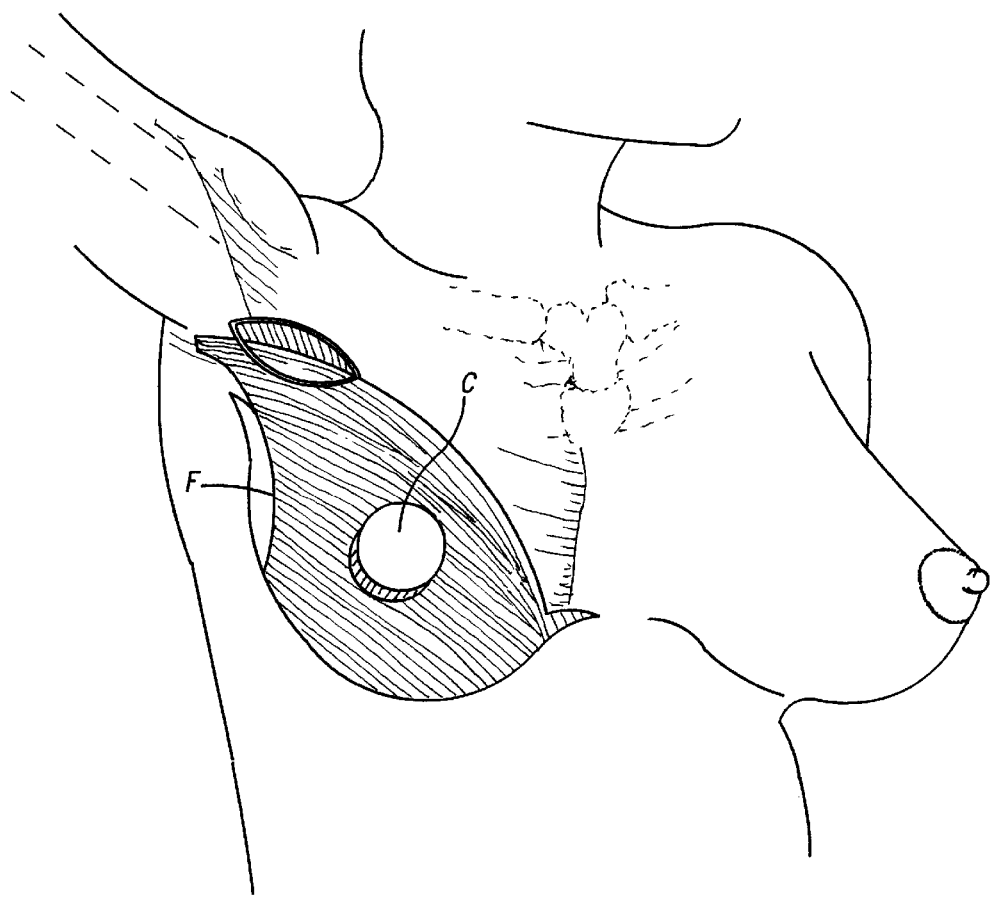
FIG. 3 illustrates the latissimus dorsi flap moved into the mastectomy defect, with the cutaneous portion (the "peg") protruding through a circumareolar incision.

FIG. 2 corresponds to a preferred flap embodiment and illustrates a latissimus dorsi muscle LD; the cutaneous peg C (that portion of the elliptically shaped cutaneous portion of the flap depicted within the dashed outline); peg C is also depicted in FIG. 3. FIG. 2 also illustrates the shape of the flap (in this embodiment a myocutaneous flap), which is depicted in broken outline on the muscle. Two fundamental cutaneous peg structures are encompassed by the present invention: a peg which has a larger cutaneous area than the maximal area of the incision opening, and a cutaneous peg which corresponds to or is smaller than the maximal area of the incision opening.

Addressing an embodiment of the peg which is larger than the maximal area of the incision opening, the area of cutaneous tissue C that will constitute the peg of the tissue flap (such as a latissimus dorsi flap) is marked at the bra line, near the border of the latissimus dorsi muscle, as shown in FIG. 2. The transverse axis of the flap is placed at the level of the inframammary fold for smaller breasts and slightly lower for more ptotic breasts to allow for an unrestricted arc of rotation to the recipient site (FIG. 2). The exterior surface of the cutaneous peg C is substantially circular, as is the incision opening, yet in this embodiment has a larger area than the incision opening. A peg generally has a larger diameter than the maximal diameter of the incision opening on the order of 0.75 to 2.0 cm, and most preferably on the order of 1.0 to 1.5 cm. Additional volume can be provided is to the reconstructed breast by de-epithelializing a skin island that is larger than the area of the incision opening. Thus, additional volume is provided by deepithelializing the cutaneous tissue adjacent to the peg, while leaving the subjacent subcutaneous tissue.

For latissimus dorsi flaps, the flap dissection plane must be anterior to the thoracodorsal bundle. (Knowlton E.W.: "Release of Axillary Scar Contracture with a Latissimus Dorsi Flap," *Plast. Reconstr. Surg.* 74:124–126, (1984)) If the dissection plane-is not anterior to the vascular bundle, the latissimus dorsi flap will die because it will be deprived of vascular supply. A portion, generally all, of the insertion of the latissimus dorsi is transacted, near the axilla, in order to provide further exposure and to increase the arc of rotation of the flap, as illustrated in FIG. 2. Although the thoracodorsal artery is transferred with the flap, lumbar perforators, for example, supply the remainder of the muscle. Then, a plane of deep dissection subjacent to the latissimus dorsi is carried out; this plane is immediately above the teres major muscle. This dissection is performed superior to the area in which the thoracodorsal artery enters.

An inferior back incision is then made. The inferior back incision is transverse and on the ipsilateral side as the mastectomy. A portion of the latissimus dorsi should be included inferior and posterior to the region of the peg. As illustrated in FIG. 3, the portion of the muscle flap F that is inferior and posterior to the peg should be sized so that it will adequately fill the breast envelope between the circumareolar incision and the inframammary skin fold. Thus, the flap F corresponds to a perimeter of the intact breast skin envelope which is at least partially defined by the inframammary skin fold. The size of the flap also allows complete coverage of an implant if required for additional volume. The inferior incision (flap donor site incision) can be begun above the peg of the flap in the superficial plane. It is preferred that subcutaneous tissue on the flap be included to provide for added tissue volume within the breast, and to act as a soft tissue buffer to lessen the effect of muscle contraction or tightening on the overlaying breast skin. It is a particular advantage that the contour irregularities of a saline implant are greatly reduced or avoided with the present invention.

Proceeding from the inferior incision, the plane of deep dissection subjacent the latissimus dorsi should be between the serratus anterior and the latissimus dorsi muscles, the dissection begun along the anterior border. (Schneider et al.: Latissimus Dorsi Myocutaneous Flap for Breast Reconstruction., *Br. J. Plast. Surg.* 30:277, (1977)) The serratus anterior is immediately subjacent to the latissimus dorsi, the surgeon should avoid picking up this muscle along with the latissimus. If the serratus anterior is raised, adherent serratus is sharply dissected from the underside of the latissimus dorsi muscle, and the serratus is simply resutured to the tissues covering the rib cage.

The inferior border of the latissimus dorsi flap is then incised. Elevation of the flap is accomplished by connecting the planes of deep dissection extending from the superior and inferior back incisions.

When properly dissected, the only structure holding the flap is the vascular connection. To prevent torsion of the vascular connection, the branch of the thoracodorsal artery leading to the serratus anterior muscle may be transacted. When moving the flap care should be taken to avoid torsion of the vessels.

The flap is moved to a subcutaneous axillary location. The back incisions are then closed and a drain is placed at the flap donor site incision. The drain should be in place approximately 10 days, since a seroma may readily form if the drain is removed too quickly. A second drain is used for the axilla and breast. The patient is then rotated to the supine position without redraping.

Although the preserved skin envelope is the main determinant of breast contour, it has now been determined that more projection can be obtained by shaping the autologous flap. Typically, the posterior border of the flap is folded under the deep surface of the muscle. A portion of subcutaneous tissue along the lateral aspect of the breast is preserved as a partition between the mastectomy and the flap donor site (FIG. 2).

The mastectomy can be performed before or after the flap isolation procedure. If a mastectomy is to be performed after flap isolation, the procedure begins with those steps achieving flap isolation, the patient is then placed in a supine position and a mastectomy is preferredly performed as indicated above with procedures amended as appreciated by one of ordinary skill in the art.

Figure 7:
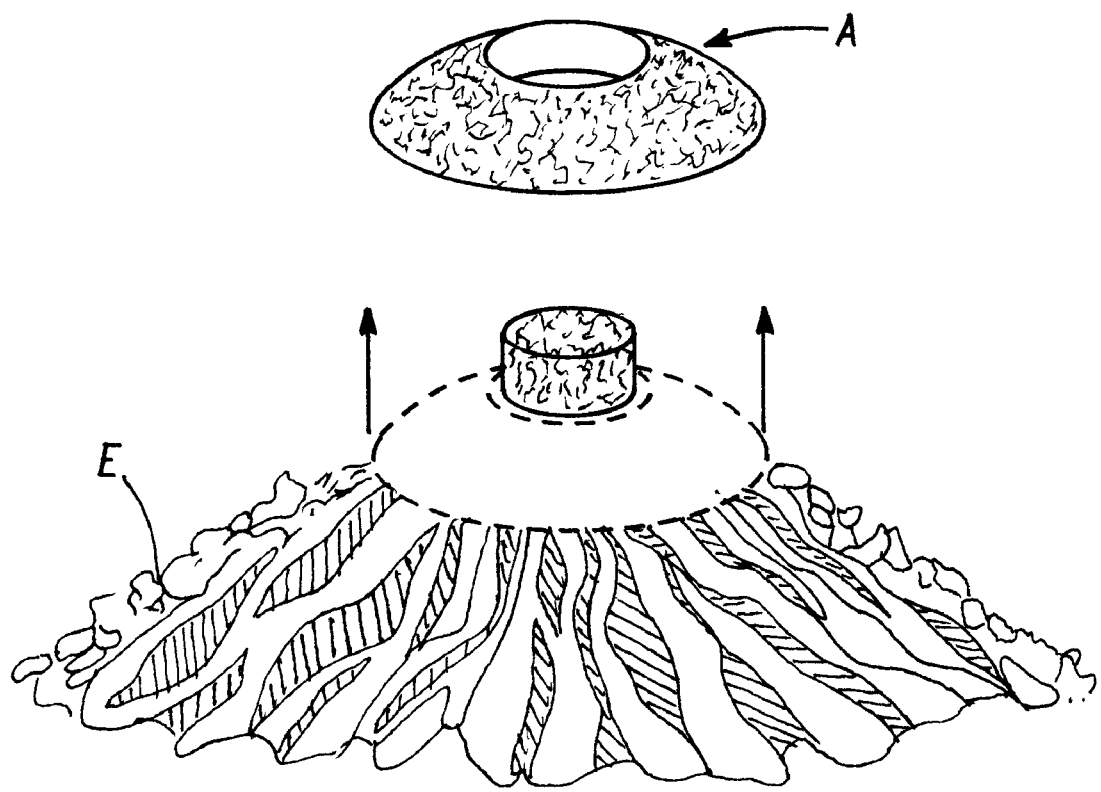
FIG. 7 illustrates harvesting of the areola from excised breast tissue.

The preferred embodiments of the invention have sufficient circulation to support immediate nipple-areolar reconstruction, and support areolar grafting if indicated. The areola A may be harvested from excised breast tissue E, as illustrated in FIG. 7. Areolar harvesting may be performed if there is no invasion of the nipple-areolar tissues. The areola is harvested as a full thickness skin graft. Harvested areola can functions as an accurate areolar donor for use in reconstruction of the patient's nipple-areolar complex.

The flap donor site and axillary incisions are closed. Approximately triangular shaped areas of skin on both sides of the skin peg excision are deepithelialized or excised so that the donor site can be closed as a linear incision.

A subcutaneous pathway is then opened between the flap (temporarily placed in the axilla) and the mastectomy defect. This pathway is sufficiently large so that postoperative edema does not occlude the vascular flow through the pedicle supplying the latissimus dorsi flap. Thereafter, the flap is delivered from the axilla into the region of the mastectomy defect. At this stage, care is again taken to verify that the vascular pedicle to the flap has not been compromised. The axillary incision can be reopened if assistance is needed in advancing the flap towards the mastectomy defect.

The inferior border of the latissimus dorsi flap is then sutured, or otherwise attached, to the chest wall along the perimeter of the mastectomy defect. If there is any tension on the flap, the insertion of the latissimus dorsi flap has not been sufficiently released. The axillary incision can then be reopened to more completely release the insertion.

If a breast implant is to be placed, a subpectoral portion of the submuscular pocket is created by releasing the inferior fibers of the pectoralis major muscle. If malignancy has invaded the lower border of the pectoralis major, excision of this tissue will not preclude use of the invention. Alternatively, an implant is placed in a prepectoral location behind the flap. In prior techniques, if the breast cancer required resection of the fascia and a portion of the pectoralis major, this limited the ability to insert a breast expander or permanent implant in a subpectoral pocket; in a preferred embodiment of the invention, with the additional inlay of latissimus dorsi, this is no longer a limitation. The present invention can still be used because of the added volume provided by use of a flap such as a latissimus dorsi myocutaneous flap.

Figure 4:
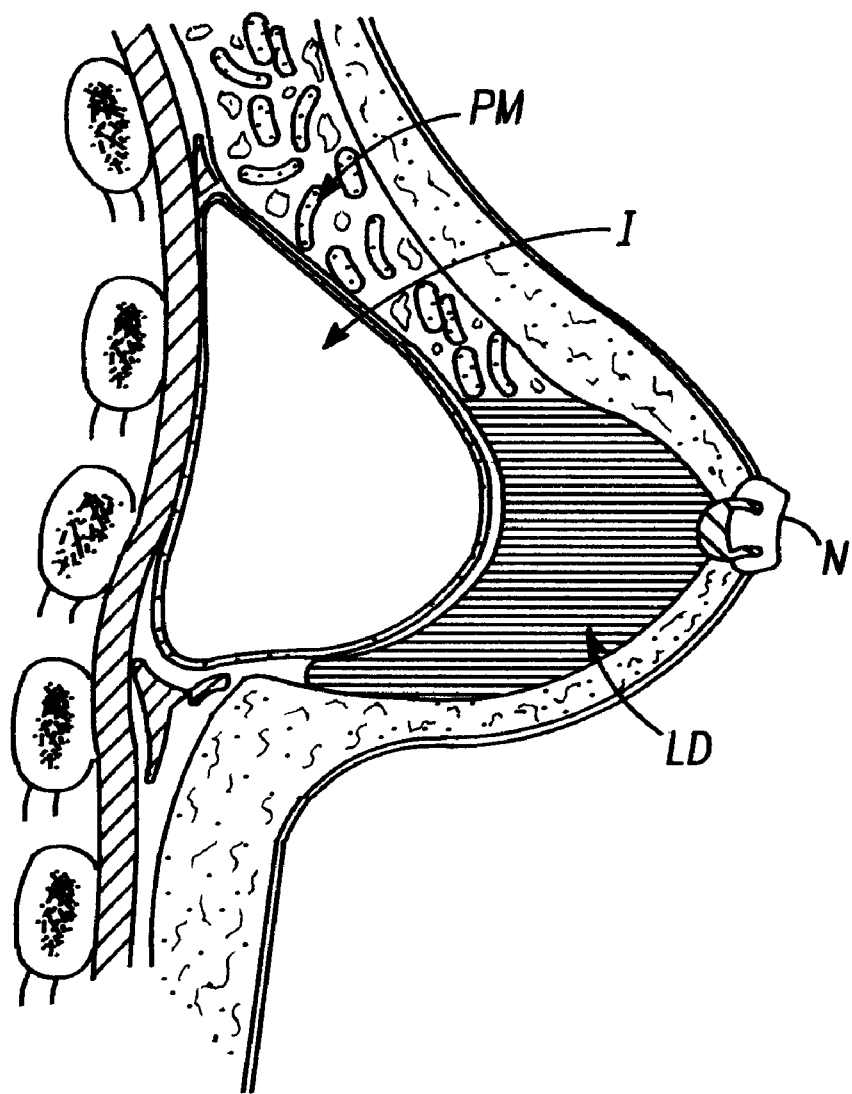
FIG. 4 illustrates a superior-inferior cross section of a reconstructed breast.

If medically indicated, a breast implant I is then placed in the submuscular pocket, as illustrated in FIG. 4. The size of the implant will, as is known to those in the art, vary greatly. An implant is only required to reconstruct large breasts. Thus, for most women, women in whom an implant is not needed, it is not necessary to dissect a subpectoral pocket. When selecting an implant size, the fact that the muscular flap will undergo atrophy must be taken into account. To best establish that the appropriate size of implant has been selected, the patient should be moved into a sitting-up position.

A drain is then inserted into the axilla, through a separate stab incision. The implant is then secured in place by suturing the superior border of the latissimus dorsi flap to the inferior border of the pectoralis major. The preferred latissimus dorsi flap and the volume of an implant which can be placed in a submuscular prosthetic pocket approximate the volume of the excised tissue. Thus, an interim breast expander is not necessary.

Figure 5:
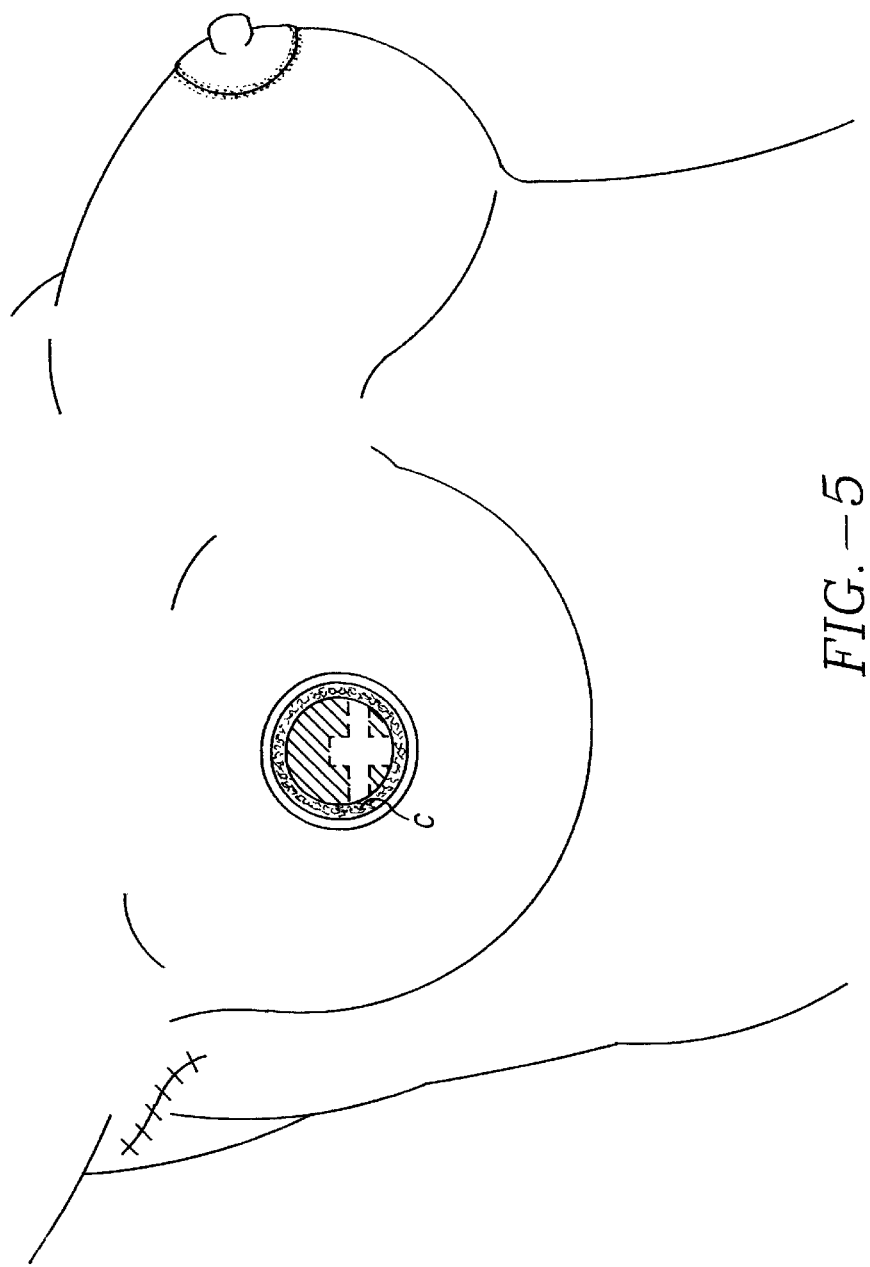
FIG. 5 illustrates markings on the skin peg that will be utilized to reconstruct a nipple via a quadruped procedure.
Figure 6:
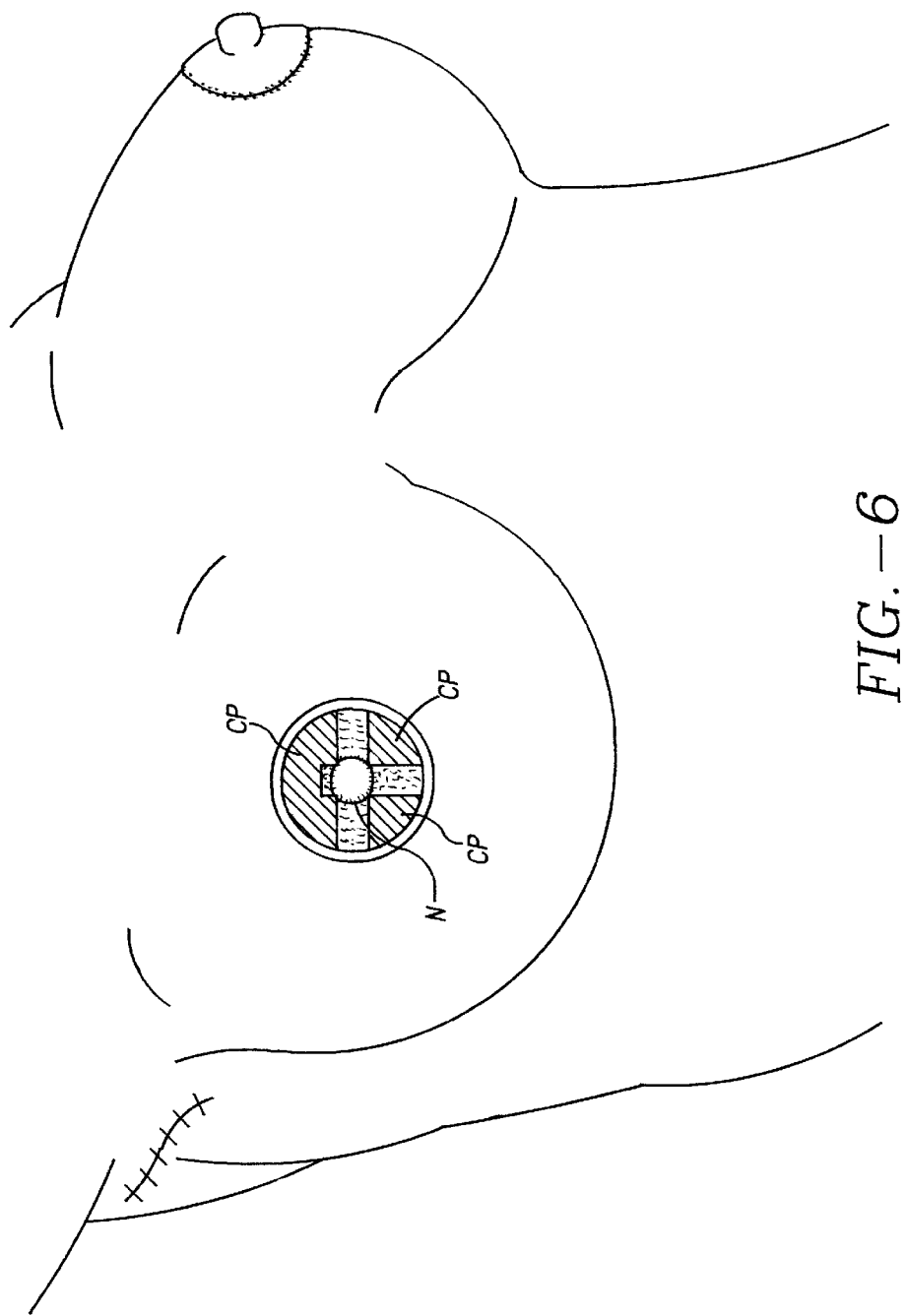
FIG. 6 illustrates the elevated quadruped nipple flaps after the peg has been sutured to the margin of the incision.

The cutaneous peg is then used to close the substantially circular defect of the excised nipple-areolar complex. Advantageously, due to the amount of circulation present in tissue flaps of the invention, such as the-preferred latissimus dorsi or TRAM flap, the nipple-areolar complex can be reconstructed immediately/contemporaneously by creating a nipple mound from the skin peg (FIGS. 5 and 6). The nipple mound can be created on the flap before the flap is moved from its donor site, or after placement of the flap in the breast. A flap should have circulation sufficient to support a reconstructed nipple-areolar complex; in light of the teaching of this invention, individuals of ordinary skill in the art will know to select flaps having sufficient intrinsic circulation or to select free flaps that are attached so as to have the appropriate level of circulation. However, if there is any question that there may not be sufficient vascular flow to the flap, the procedure can be terminated at this stage. In accordance with the invention, the flap need not be used to create any aspect of a nipple-areolar complex, the flap must be selected so as to be understood by those of ordinary skill in the art to be usually capable of supporting a nipple-areolar reconstruction. Individual anatomical variation whereby a flap that would usually support a reconstruction will not support a reconstruction can still fall within the invention; it will not, however, lead to the preferred result. If for some reason the surgery must be halted, the invention encompasses that the procedure terminates before reconstructing the nipple-areolar complex. The margin of the peg can be sutured or otherwise attached to the margin of the breast skin envelope.

In one embodiment of the invention, a cutaneous peg which is larger than the maximal area of the incision opening is used to recreate the nipple areolar complex. Placing the cutaneous peg into an opening having a smaller area than the peg produces the advantageous effect that the peg protrudes from the surface of the breast: enhanced nipple-areolar projection is obtained thereby.

Enhanced nipple areolar projection is also obtained by use of an embodiment of the cutaneous peg which corresponds to or is smaller than the area of the incision opening. To achieve such projection, the incision area is effectively decreased; for example, purse-string suturing is used when attaching the peg to the margin of the incision opening.

Moreover, in each embodiment of the peg, enhanced projection is also achieved due to the elastic recoil and scar contraction qualities of the breast skin surrounding the peg. Advantageously, skin elastic forces and scar contraction forces are manifest during the healing process.

The TRAM flap is an alternate source of a tissue flap for use in the invention. TRAM flap embodiments of the invention frequently do not require use of any artificial implant. The TRAM flap is harvested either as a single pedicle (one rectus muscle) or double pedicle (both rectus muscles) flap. Free microvascular flap harvesting can also be employed in accordance with the invention. The muscle may be vertically split to preserve a portion of the rectus abdominis. Most of the skin and fat are harvested below the umbilicus. The amount of abdominal tissue that is removed is approximately the same amount as in a standard abdominoplasty ("tummy-tuck"). The individual steps of the TRAM embodiment of the invention comport with standard medical practice.

The blood supply to the flap can be kept intact and moved with the flap or the flap can be moved as a free flap and be reattached at the chest wall site by vascular techniques known in the art.

With immediate reconstruction, the circumareolar mastectomy is usually performed before flap isolation.

In general, the steps of a TRAM-based embodiment are as follows: The patient is initially positioned in a supine position. The chest and abdomen are prepped and draped in sterile fashion. The rectus abdominis muscle of the flap supports the superior epigastric artery and vein which supply blood to the island of muscle, skin, and fat that is transposed. The cutaneous portion of the flap is used to create the nipple-areolar complex. The complex can be created either before or after the flap is moved to the recipient site. As disclosed herein, it is preferred that the cutaneous portion be supplied by perforator vessels.

The reconstruction is started with a transverse incision just above the umbilicus and extending hip to hip. A plane of dissection is developed through the subcutaneous tissue to the rectus abdominis fascia in the epigastric area. The dissection is carried up to the costal margin. A tunnel is developed from the donor site, over the sternum, to the mastectomy defect. Two parallel cuts in the rectus fascia are made from the costal margin to the transverse skin incision. The umbilicus is circumscribed and a lower transverse incision is made hip to hip, connecting with the upper incision. A large flap of skin, subcutaneous tissue and muscle is isolated by elevating the flap in a lateral to medial direction off the abdominal wall fascia to the rectus sheath. Myocutaneous perforators through the rectus sheath are identified and preserved as the feeding vessels to the skin and subcutaneous tissue of the flap. The perforator vessels are important in the preferred embodiment of the TRAM flap-based procedure. The vertical fascial cuts are then extended inferiorly and the underlying rectus muscle is harvested with the superior and inferior epigastric arteries and veins.

For a pedicled flap, the superior epigastric artery is used and the inferior epigastric artery is ligated. For a free flap the inferior epigastric artery is usually used as the circulatory conduit.

A substantially circular "peg" of skin corresponding in shape to the perimeter of the excised nipple-areolar complex is preferably designed over a rectus musculocutaneous perforator. Designing the location of the nipple-areolar reconstruction over perforator vessels facilitates immediate reconstruction of the nipple-areolar complex. Use of a double pedicle flap can also augment circulation. The skin on the TRAM flap that is not used in the creation of the nipple-areolar complex is removed, and attachment of the flap to the mastectomy defect is performed.

The rectus fascia and muscle defects are repaired, and the lower abdominal incision is closed similar to an abdominoplasty with a transverse incision running hip to hip below the umbilicus. The retained umbilicus is brought out through a small separate incision in the midline above the transverse incision.

A delayed embodiment of the invention comprising a TRAM flap involves similar steps of TRAM flap creation, however these steps occur in a subsequent procedure, typically following expansion of the breast envelope. Delayed reconstruction is addressed in greater detail below. In delayed embodiments of the invention, no isolation of a tissue flap is performed at the time of the mastectomy operation. At the end of the mastectomy operation (or at a subsequent stage), a temporary breast expander is placed and the incision is closed with a straight line incision. The mastectomy can comprise a circumareolar or a standard modified radical mastectomy. As appreciated by those of ordinary skill in the art, the flap isolation procedures outlined herein with regard to contemporaneous reconstruction are performed in a separate stage some period of time following a mastectomy, and generally after breast expansion. Flap isolation takes place after the breast is sufficiently expanded so as to approximate the volume of the contralateral breast. After breast envelope expansion, a circular incision is made. As discussed in greater detail herein, the incision generally has a maximal non-stretched diameter about 1.5 cm less than the diameter of the contralateral nipple-areolar complex. The smaller nipple-areolar recipient site of the breast envelope is preferably stretched to accommodate the larger reconstructed nipple-areolar complex. Subsequent elastic recoil and scar contraction facilitate the result of enhanced nipple-areolar projection in accordance with the invention.

Alternatively, with a delayed latissimus dorsi procedure, the tissue flap is then dissected, and transferred to the axilla. The patient is then placed in a supine position, the breast expander is removed through a substantially circular incision corresponding to the margin of an areola. The flap is then moved to the-breast skin envelope as previously described, and nipple-areolar reconstruction with peg embodiments described herein is performed.

In immediate or delayed procedures, the nipple-areolar complex is created either at the flap donor site or after the flap is moved to the recipient breast.

A preferred nipple reconstruction is the "bow tie" technique of Knowlton. The Knowlton "bow tie" procedure is a development beyond principles used in "star" nipple reconstruction. (Anton, M. A., et al., *Perspect. Plast. Surg.* (1991) 5:67) In the Knowlton procedure, the vertical limbs of the "bow tie" are designed as rectangles and extend to the perimeter of the "peg" flap. (FIG. 2) In an embodiment of the Knowlton "bow tie" procedure, the vertical limbs of the flap are designed as rectangles which are larger distally and narrower more proximally (proximal and distal defined relative to the connection of a rectangular flap to the nipple flap).

Figure 9:
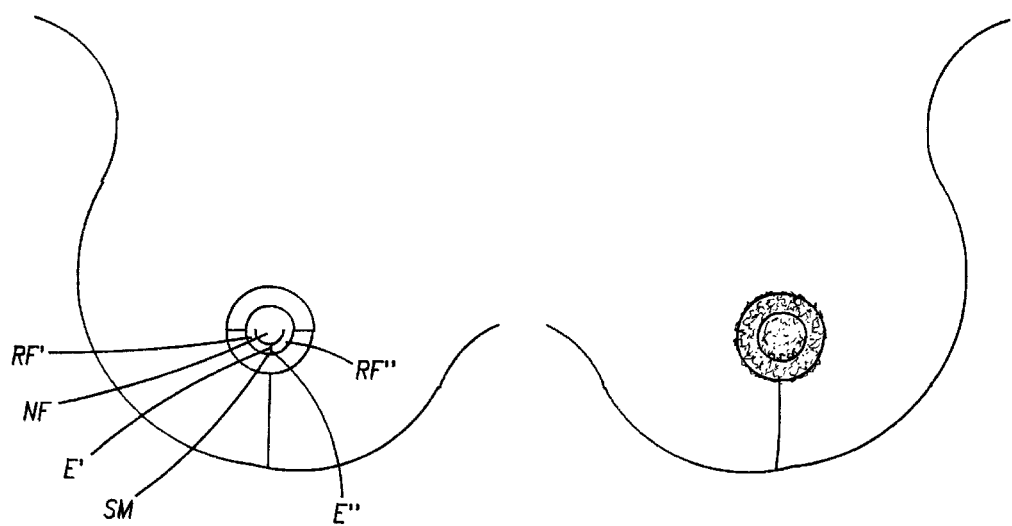
FIG. 9 depicts the resulting incisions following the surgery depicted in Example 2, and depicts use of the Knowlton bow tie nipple-areolar reconstruction.

Thus, to create a bow tie reconstruction, the two rectangular flaps (RF' and RF") and a rounded nipple flap (NF) are dissected. (FIG. 2) The flaps are preferably dissected so as to include a variable amount of subcutaneous tissue, to provide volume to the reconstructed nipple. Referring to FIGS. 2 and 9, closure of the nipple flap donor site occurs by suturing of the rectangular flaps to the margin of semi-circular incision, and advances the donor semi-circular incision (semicircular margin SM). In a preferred embodiment with creation of laterally wider rectangular flaps, closure of the divergent, laterally wider donor sites produces a result of further enhances the conical shape of the reconstructed areola. As depicted in FIG. 9, the distal ends (E' and E") of the rectangular nipple flaps are sutured together resulting in placing of a margin (the inferior margin) of each rectangular flap in close approximation to the inner margin of the underlying semi-circular margin SM (the nipple flap donor site), and resulting in placing of a margin (the superior margin) of each rectangular flap beneath the nipple flap NF. The margin of nipple flap NF is sutured to the superior margins of the rectangular flaps and the semicircular margin is sutured to the inferior margins of the rectangular flaps to create a projecting nipple. The perimeter of the reconstructed nipple-areolar complex is then circumscribed with an appropriately sized circular template to facilitate obtaining a substantially circular shape for the reconstructed complex. Using the circular template, the skin outside of the "peg" flap is de-epithelialized (FIG. 3) to create a reconstruction with a perimeter that corresponds to the shape of an areolar perimeter. A variation is to use the harvested areola as a full thickness skin graft over a de-epithelialized areolar portion of the "peg."

To prevent contour distortion upon closing the peg donor site, the surgeon can undermine adjacent skin near the peg donor site at the time of flap elevation. Such undermining can be performed when creating a nipple-areolar complex at the donor site, and serves to relieve any tension that could result in contour distortion.

Alternatively, a nipple N can be reconstructed from a superiorly pedicled quadruped flap, as known in the art. Alternative methods of nipple-areolar reconstruction are known to those skilled in the art. Such methods include nipple mound reconstruction with quadruped, triped or biped pedicled flaps; or with subcutaneously pedicled quadruped or triped flaps. Nipple projection can also be obtained through the use of ear-cartilage, or the use of a subcutaneously implanted nipple prosthesis.

With immediate reconstruction, an areolar graft can be sutured in place. This tissue can be harvested from the patient's own excised nipple areolar complex. Rather than discarding the areola A, as is commonly done, the areola can be defatted (as illustrated in FIG. 7), and placed as a full-thickness skin-graft to the deepithelialized peg; the deepithelialized peg is created, for example, with removal of the cutaneous portions CP of the peg which were not used to create a nipple mound (as illustrated in FIG. 6). The highly vascularized nature of subject cutaneous flaps allow grafting to occur contemporaneously. Alternative skin graft donor sites for the areola are known to those skilled in the art. For example, the areola can be reconstructed with either full thickness or split thickness skin grafts from the thigh, groin, labia, post-auricular skin, and any other readily available skin graft donor sites. Approximately six to eight weeks post-operatively, the patient can undergo tattooing or micropigmentation of the nipple.

Nipple recreation may occur, with either contemporaneous or delayed surgeries, without additional skin grafting. If the nipple is raised from the area of the cutaneous peg without additional skin grafting, subsequent tattooing will occur over the entire nipple-areolar complex, rather than just to the nipple area.

For women with large or ptotic breasts, a breast reduction and/or nipple-areolar repositioning may be used in combination with the tissue flap breast reconstruction of the present invention. A breast reduction and/or nipple-areolar repositioning can be performed according to procedures known to those of skill in the art. For example, a breast reconstruction can be performed by a Wise pattern (keyhole) skin reduction. In such cases, the contralateral breast would also undergo a similar Wise pattern breast reduction. An appropriately sized tissue flap is used to substitute for the missing breast tissue on the mastectomy side; the reconstructed breast corresponds to the volume of the size-reduced contralateral breast. Thus, both breasts would have typical breast reduction/nipple repositioning incisions. In a preferred embodiment, the nipple-areolar complex at the mastectomy site is reconstructed with the circular peg of a latissimus dorsi flap, while on the contralateral breast the nipple-areolar complex is transposed to the same level as the peg-derived nipple of the mastectomy site. In contrast, women with even moderately ptotic breasts would not require correction of the contralateral side, since the skin on the mastectomy side remains completely intact and the volume of the breast reconstructed with the subject tissue flap corresponds to the volume of the contralateral breast.

Accordingly, a preferred embodiment of the tissue flap procedure comprises a cutaneous peg that serves as an elevated platform upon which the nipple-areolar complex is reconstructed. A reconstructed breast results that more accurately replicates the three dimensional projection of a normal breast, including the presence and projection of the nipple-areolar complex. As disclosed herein, use of a peg embodiment which is larger than the area of the incision opening, or a peg embodiment of the peg which corresponds to or is smaller than the area of the incision opening together with incision opening diminution procedures have each resulted in enhanced nipple-areolar projection. Such breast contour and projection results have not been available with former procedures.

Advantages of the post-circumareolar mastectomy total, immediate reconstruction embodiment of the procedure of the present invention include camouflaging of the scar around the perimeter of the nipple, and the improved projection of the reconstructed nipple-areolar complex. Further, with a preferred latissimus dorsi embodiment of the procedure there is very limited muscular function loss consequent to the movement of the flap, since the teres major compensates for the loss of the latissimus dorsi muscle.

Delayed Procedures

Delayed procedures define another preferred category of embodiments of the invention. For patients requiring a standard modified radical mastectomy, delayed/multi-stage reconstruction is performed in accordance with the invention. With delayed reconstruction, a temporary subcutaneous or submuscular breast insert such as a breast expander is usually inserted in the breast envelope. The expander is preferably subcutaneous. Subcutaneous expanders tend to cause less pain during the expansion process. Moreover, surgical placement of a subcutaneous expander is less complex process than a process of creating a submuscular pocket necessary for placement of a submuscular expander.

If after a mastectomy, a subcutaneous expander is placed, a switch can occur to allow placement of a permanent submuscular implant. This process is referred to as the "hinge" procedure. To achieve the submuscular placement, the scar capsule which formed around an insert such as a subcutaneous expander or a subcutaneous breast implant is utilized. Accordingly; the posterior portion of the scar capsule is elevated off the pectoralis major and moved laterally, so that it can be attached to the inferior margin of the pectoralis major muscle; thereby effectively creating an enlarged submuscular compartment while avoiding the pain commonly associated with submuscular expansion. The scar capsule continues to be connected to its vasculature by an attachment to the serratus anterior at the lateral margin of the capsule. The pectoralis major is not thinned or attenuated during the expansion phase; this feature is relevant in that the muscle can then be used to cushion the margins of any saline implant which is subsequently placed in the effectively enlarged submuscular pocket. Moreover, since the scar capsule is moved, the otherwise relatively firm connections between the skin and anterior portion of the scar capsule, and between the posterior portion of the scar capsule and underlying muscle are eliminated. The breast skin and the underlying smooth surface of the anterior capsule slide relative to the submuscular pocket. Thus, any pressures exerted by an implant can be diffused by shifting of the muscle and skin relative to one another, thereby avoiding transmission of the forces to the skin as a surface contour distortion.

The ability to create an effectively enlarged. submuscular pocket in a procedure comprising use of a subcutaneous scar capsule provides options in the performing of the reconstruction in accordance with the invention and provides options for women who may wish to undergo repositioning of a permanent implant. Implant repositionings often occur after a women decides that she wants to have a silicone gel implant removed and replaced with a saline implant. Frequently, the women who have implants have minimal breast tissue (this feature providing motivation for placement of the implant); the paucity of tissue enhances the possibility that implant contours are transferred to the skin surface. The present method for creating an effectively enlarged submuscular pocket is used with implant repositioning to diminish the transmission of implant contours to the skin surface. By placing the repositioned implant in a submuscular location the intervening muscle and scar capsule cushion and disperse the contour impressions before they are transmitted to the skin surface.

Placement of a breast expander (subcutaneous or submuscular) can be performed concurrently with the mastectomy or as a delayed first stage. Usually, a textured expander with an incorporated valve is used. If indicated, repositioning of the contralateral breast is typically performed at the time of expander placement. Over-expansion of the native breast envelope is generally indicated, especially along the inferior pole. In a preferred embodiment, a subsequent stage involves the removal of the expander, the creation of an autologous "peg" tissue flap, and the insertion of the flap into the breast envelope. With the latissimus dorsi embodiment of the flap, the physician should determine whether the patency of the thoracodorsal vessels may have been compromised by pre-existing radiation damage or surgical trauma during a previous axillary lymph node dissection. Comparison of the Doppler signature to the contralateral thoracodorsal bundle facilitates this analysis. A color duplex scan will provide a more detailed study of flow characteristics.

Generally, the nipple-areolar complex is created at the flap donor site, the nipple is created in accordance with known medical procedures such as by the presently preferred "bow tie" technique.

A small 2.5 cm diameter circular recipient site on the breast is created for a woman who has an areolar diameter of about 4.0 cm. If needed, multiple radial capsulotomies along the inferior pole of the breast are performed to provide additional ptosis. A segmental capsulectomy at the superior pole provides additional room for postoperative flap edema; otherwise, compression atrophy of the flap may occur. The recipient site is stretched to approximately 4.0 cm to receive the cutaneous portion of the tissue flap. Stretching of the recipient site facilitates the preferred outcome of the procedure since during healing skin elastic forces and scar contraction forces enhance nipple-areolar projection. In a preferred embodiment, a nipple-areolar complex was reconstructed on the cutaneous portion prior to placement of the flap in the breast. Regardless of breast or incision size, a 1.0 cm to 1.5 cm differential is typically sufficient to achieve the desired projection. With the present method, a net gain in the skin envelope occurs without the pigmentary discrepancy or double-tier scar of a standard flap reconstruction.

For patients who require a standard modified radical mastectomy or who desire a delayed reconstruction, a two-stage method of autologous reconstruction with the "peg" tissue flap achieves several benefits relative to prior procedures: Contour irregularities consequent to the use of saline implants are avoided, as is the pigmentary discrepancy and double-tier scar of a standard flap reconstruction.

The concentric recoil of the breast skin, such as occurs by means of elastic forces and/or scar contraction forces, projects the entire nipple-areolar complex to an elevated position.

EXAMPLES

Example 1

The patient was a 40 year old multiparous woman with B-cup size breasts that were moderately ptotic. She presented with a 3.0 cm invasive ductal and multifocal carcinoma in situ of the left breast. The patient initially underwent a combined single stage skin preservation mastectomy with axillary lymph node dissection and an autologous "peg" latissimus dorsi flap reconstruction. The nipple-areolar complex was reconstructed at the initial stage. The nipple-areolar complex was subsequently revised with the "bow tie" technique. The patient's postoperative course was uneventful, and the projection and general aesthetics of the reconstructed nipple-areolar complex were much improved relative to their state prior to the revision surgery.

Example 2

Figure 8:
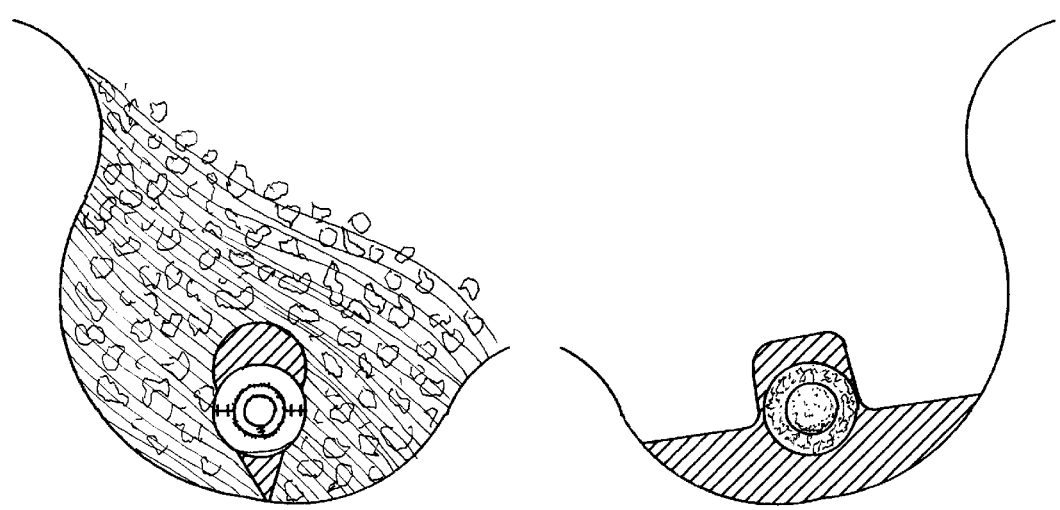
FIG. 8 depicts an inferior vertical wedge resection to crease the circumference of the breast skin recipient site on the right breast, and depicts a "Wise" keyhole reduction of the left breast.

The patient was a 62 year old, moderately obese female with large pendulous breasts. An extensive ductal carcinoma in situ of the right breast was present. The patient underwent a combined skin preservation mastectomy with lymph node sampling and autologous "peg" latissimus dorsi flap with nipple-areolar reconstruction. The left breast was reduced with a standard "Wise" keyhole approach. The right reconstructed nipple-areolar complex was repositioned with an excision of a superior semilunar ellipse. To reduce the size of the incision opening relative to the size of the cutaneous peg, an inferior vertical wedge resection decreased the circumference of the breast skin recipient site (FIG. 8). The resulting incisions are depicted in FIG. 9. The entire procedure was performed in a single stage. A donor site seroma resolved after several aspirations. Excellent nipple-areolar contour and projection of the right breast resulted.

Example 3

The patient was a fifty-four year old woman who had a bilateral breast augmentation twenty years prior to cancer surgery. A 1.0 cm palpable mass in the left breast that was negative on mammography proved to be a ductal carcinoma on biopsy. The patient had a single stage procedure that consisted of mastectomy with axillary lymph node dissection; immediate reconstruction was accomplished with an autologous tissue flap, including creation of the nipple-areolar complex. The nipple was reconstructed with the Knowlton bow tie technique. The projection of the nipple-areolar complex was enhanced over time due to effects of scar contraction and skin elastic forces. The breast implant was removed on the reconstructed side. The gel implant in the right breast was replaced with a saline prosthesis. This patient had a larger peg than the maximal unstretched incision plane area in order to achieve enhanced projection of the reconstructed nipple-areolar complex. The projection was further increased during healing, pursuant scar contraction.

The patient is to have a "hinge" procedure done to create an effectively enlarged submuscular pocket which will lessen the contour effects created by the margins of the saline implant.

Example 4

The patient presented for revision of a three year old breast reconstruction. The patient was a 51 year old woman who had undergone a modified radical mastectomy for ductal carcinoma of the right breast. An initial reconstruction with a temporary expander and a permanent saline implant resulted in the contour irregularities that are common with this prosthesis. Three years later, the patient's reconstruction was revised in two stages. A temporary expander was re-inserted for additional ptosis of the right breast, and the left breast was repositioned. Creation of an autologous "peg" flap for use in reconstructing the nipple-areolar complex was performed in a subsequent stage. The autologous "peg" flap was used that had a cutaneous portion with a diameter approximately 1.5 cm greater than the diameter of the incision opening. During post-surgical healing, the scar contraction and elastic recoil of the breast skin at the recipient site enhanced the projection of the entire nipple areolar complex and produced a net gain in the size of the breast envelope. Excellent nipple-areolar projection resulted pursuant to the procedure.

Example 5

The patient was a 48 year old woman with a previously diagnosed ductal carcinoma of the right breast who underwent a standard modified radical mastectomy with a transverse elliptical resection of skin. The skin resection included the nipple areolar complex. The patient had a typical scar and deformity across the chest. The patient's delayed reconstruction consists of an initial insertion of a subcutaneous expander and a left breast reduction. Following a 4-month interval of serial expansion of the right breast envelope, an autologous "peg" procedure with a TRAM flap is performed. Improved projection of the reconstructed nipple areolar complex is provided by stretching a smaller circular recipient site and inserting a larger reconstructed nipple-areolar complex (peg) from the TRAM flap. The peg portion of the flap being selected to be over perforator vessels. Upon healing, scar contraction and elastic recoil of the breast skin at the recipient site enhance projection of the entire nipple areolar complex.

The tissue flap procedure of the invention is performed either as a single-stage, total and immediate breast reconstruction, or as a delayed reconstruction. The tissue flap can be a free flap or a flap attached via its native vascular connections; the tissue flap can comprise a muscular component and be termed a myocutaneous flap. Frequently, the procedure eliminates the trauma and costs of procedures to size-adjust the contralateral breast. For a single-stage reconstruction, patient morbidity and health care costs are significantly reduced relative to a multi-staged breast reconstruction. Thus, with either immediate or delayed embodiments of the invention there are cost savings together with improved aesthetic and morbidity-related results as compared to former procedures.

Although the present invention has been particularly described with regard to open surgical techniques, other surgical techniques are within the scope of the invention. For example, endoscopic dissection of a cutaneous peg flap and the mastectomy site can be performed. Although certain embodiments of the procedure have been set forth, these embodiments are not to be construed as limiting the invention. Other medical techniques and sequences of performing the steps of the procedure can be utilized, as will be known to those of skill in the art. The procedure of the present invention is disclosed herein. Procedures that correspond to the present disclosure are addressed in the videotape "The Peg Latissimus Dorsi Flap Procedure: A One-Stage Breast Reconstruction on Video: Autologous Reconstruction Immediate and Delayed" (Medial Media Productions, Sausalito, Calif., 1994), which is incorporated by reference herein. The videotape is directed to skilled artisans, and addresses preferred embodiments and the best mode for performing a procedure of the present invention. It is understood that the scope of the invention is limited only by the claims.

It must be noted that as used herein and in the appended claims, the singular forms "a," "and," and "the" include plural referents unless the context clearly dictates-otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications mentioned herein are incorporated by reference herein, to describe and disclose specific information for which the publication was mentioned.

What is claimed is:

1. A surgical method, comprising the contemporaneous steps of:
   performing a mastectomy on a breast through a substantially circumareolar incision, the incision defining a maximal unstretched incision plane area; and,
   surgically utilizing a cutaneous flap or a non-latissimus dorsi myocutaneous flap comprising placing the cutaneous portion of the flap within the incision plane area.

2. The method of claim 1 wherein the flap has a cutaneous peg which has a surface area greater than the maximal unstretched incision plane area defined by the incision, or wherein cutaneous portion of the flap has a surface area equal to or less than the maximal unstretched incision plane area and comprising reducing the incision plane area so as to be less than the area of the cutaneous portion of the flap.

3. The method of claim 1 wherein the flap comprises sufficient vascularization to support a contemporaneous nipple-areolar reconstruction.

4. The method of claim 3 further comprising a step of creating a nipple-areolar complex with a portion of the cutaneous portion of the flap.

5. A surgical method, comprising the steps of:
   performing a surgical procedure comprising performing a mastectomy via an incision on a breast;
   closing the breast incision; and,
   performing a subsequent surgical procedure comprising surgically utilizing a tissue flap comprising a cutaneous portion having a perimeter that corresponds in shape to the perimeter of an areola and wherein the flap can routinely support creation of a nipple-areolar complex.

6. The method of claim 5 further comprising a step of placing a breast expander.

7. The method of claim 6 wherein the step of placing a breast expander comprises occurring during the surgical procedure that comprises performing a mastectomy.

8. The method of claim 5 wherein the step of surgically utilizing a flap further comprises creating a nipple-areolar complex.

9. The method of claim 5 wherein the surgical procedure that comprises surgically utilizing a tissue flap further comprises creating a substantially circular incision having a shape corresponding to the perimeter of an areola, the substantially circular incision defining a maximal unstretched incision plane area, and wherein the cutaneous portion of the tissue flap has a surface area greater than the maximal unstretched incision plane area, or wherein cutaneous portion of the tissue flap has a surface area equal to or less than the maximal unstretched incision plane area and comprising reducing the incision plane area so as to be less than the area of the cutaneous portion of the tissue flap.

10. A method for creating an effectively enlarged submuscular compartment for use in post-mastectomy breast reconstruction or for breast implant repositioning, comprising steps of:
    placing a subcutaneous breast insert;
    removing said insert after a scar capsule has formed around the insert; and,
    attaching the scar capsule to a pectoralis major muscle defining a submuscular space or capable of defining a submuscular space, whereby an effectively enlarged submuscular compartment is created.

11. The method of claim 10 wherein the breast insert is a breast implant or is a breast expander.

12. A method for recreating a nipple-areolar complex with conical projection comprising steps of:
    dissecting a nipple flap and two rectangular flaps on a tissue flap, the two rectangular flaps connected at their respective proximal margins to the nipple flap, the rectangular flaps connected on opposite sides of the nipple flap; and,
    suturing the nipple flap to the two rectangular flaps to create a reconstructed nipple-areolar complex.

13. The method of claim 12 wherein the dissecting step comprises dissecting rectangular flaps wider distally than their respective widths at their proximal connections.

14. The method of claim 12 wherein the dissecting step comprises including subcutaneous tissue beneath the nipple flap or one of the rectangular flaps, thereby providing increased volume to the reconstructed nipple.

15. The method of claim 12 further comprising a step of circumscribing a perimeter of the reconstructed nipple-areolar complex with a substantially circular template, to facilitate obtaining a substantially circular shape for the reconstructed complex.

16. The method of claim 15 further comprising a step of excising cutaneous tissue beyond the perimeter of the nipple-areolar complex.

* * * * *